United States Patent

Ohi et al.

[11] Patent Number: 5,110,741
[45] Date of Patent: May 5, 1992

[54] AERATION APPARATUS FOR THE CULTURE OF MAMMALIAN CELLS

[75] Inventors: Kiyomoto Ohi, Nara; Shin Shimizu, Kyoto, both of Japan

[73] Assignee: Toyo Boseki Kabushiki Kaisha, Osaka, Japan

[21] Appl. No.: 520,973

[22] Filed: May 9, 1990

Related U.S. Application Data

[63] Continuation of Ser. No. 167,340, Mar. 14, 1988, abandoned.

[30] Foreign Application Priority Data

Mar. 18, 1987 [JP] Japan .................. 62-65362

[51] Int. Cl.$^5$ .................. C12M 3/02; C12M 1/06
[52] U.S. Cl. .................. 435/284; 435/286; 435/311; 435/313; 435/315; 435/818; 261/122
[58] Field of Search ........ 435/311, 313, 315, 284–286, 435/818; 422/45, 46, 48; 261/104, 122, DIG. 28; 210/321.67, 321.79, 321.8, 321.88, 321.89

[56] References Cited

U.S. PATENT DOCUMENTS

| | | | |
|---|---|---|---|
| 3,883,393 | 5/1975 | Knazele et al. | 435/284 |
| 4,075,100 | 2/1978 | Furuta et al. | 210/321.8 |
| 4,620,965 | 11/1986 | Fukusawa et al. | 210/321.8 X |
| 4,639,353 | 1/1987 | Takemura et al. | 422/48 X |
| 4,647,539 | 3/1987 | Bach | 435/240.25 X |
| 4,649,114 | 3/1987 | Miltenburger et al. | 435/284 |

FOREIGN PATENT DOCUMENTS

60-234580 11/1985 Japan.
61-25477 2/1986 Japan .................. 435/284

OTHER PUBLICATIONS

Production of Cell–Derived Products: Virus and Interferon*, by A. J. Sinskey, R. J. Fleischaker, M. A. Tyo, D. J. Giard and D. L. C. Wang, Annals New York Academy of Science, 1981, pp. 47–59.

An Experimental Study in the Use of Instrumentation to Analyze Metabolism and Product Formation in Cell Culture by R. J. Fleischaker, Jr., Submitted to the Department of Nutrition and Food Science on May 21, 1982.

Oxygen Demand and Supply in Cell Culture by R. J. Fleischaker, Jr. and A. J. Sinskey, European Journal of Applied Microbiology and Biotechnology, 1981, pp. 193–197.

*Primary Examiner*—Robert J. Warden
*Assistant Examiner*—William H. Beisner
*Attorney, Agent, or Firm*—Leydig, Voit & Mayer

[57] ABSTRACT

An aeration apparatus for the culture of mammalian cells comprises a plurality of bundles composed of thin-walled narrow tubes made of gas permeable material, a first head for introducing a gas to the bundles through a gas connector and a second head for removing gas from the bundles through a gas connector, both the first head and second head providing flow communication to and from the bundles, respectively, the apparatus being positioned in a culturing vessel so that the bundles are in a slackened state.

2 Claims, 4 Drawing Sheets 5,110,741

AERATION APPARATUS FOR THE CULTURE OF MAMMALIAN CELLS

This application is a continuation of application Ser. No. 07/167,340 filed Mar. 14, 1988, now abandoned.

BACKGROUND OF THE INVENTION

1. Field of the invention

This invention relates to an aeration apparatus for the culture of mammalian cells. More particularly, it relates to an aeration apparatus that supplies the aeration that is necessary and sufficient for the growth of the cells when large-scale culture of mammalian cells is being done, so that the said cells can be cultured under appropriate environmental conditions.

2. Description of the prior art

Conventional culture of mammalian cells is done, for example, in the culture apparatus 1 shown in FIG. 2. This culture apparatus 1 has a culture vessel 6 with impeller 3. The culture vessel 6 is provided with an air supply inlet 4 and an exhaust outlet 5. When mammalian cells are to be cultured with the use of this apparatus, culture broth 2 that contains mammalian cells is placed inside the culture vessel 6, and air, air enriched with oxygen, or very pure oxygen (below, all referred to as 'air') is supplied, while the impeller 3 causes agitation. The air supplied is taken in through the surface of the culture broth 2 that is being agitated, supplying air to the mammalian cells that are in the culture broth 2.

With such an apparatus, when the volume of the culture vessel 6 is relatively small (about 100–1000 ml), the supply of air is adequate, but when the volume of culture vessel 6 is large (for example, 500–1000 liters), sufficient air is not supplied to the culture cells. That is, when culture is on an industrial scale, the ratio of the surface area to the volume of fluid in culture vessel 6 becomes small, and an aeration system by means of the diffusion of air does not provide the necessary and sufficient amount of air for the growth of the cells.

A number of means have been used for the supply of the necessary and sufficient amount of air for the growth of mammalian cells being cultured on an industrial scale (that is, for the purpose of increasing the volumetric oxygen-transfer coefficient.

The method for aeration of culture vessels on an industrial scale that is most widely used today is a direct method for air supply by means of bubble aeration and agitation with an air-blowing nozzle introduced into the culture broth. In this method, the tip of the hole in the air-blowing nozzle is provided with an orifice or a sintered filter or the like, and the diameter of the bubbles of air is made as small as possible, so that the general capacity coefficient for oxygen in the culture broth becomes as large as possible.

In the method for air supply by means of bubble aeration and agitation, the bubbling of the culture broth becomes pronounced. The reason is that when mammalian cells are to be cultured, there are proteins such as serum, etc., in the culture broth, and the said proteins act as surface-active agents. The bubbling of the culture broth inhibits the growth of the cells and decreases the production of product produced by the cells, when the vessel is filled with many bubbles.

In another method for the effective supply of air to culture cells, the partial pressure of oxygen can be increased within the upper limit above which cytotoxicity would occur, causing an increase in the volumetric oxygen-transfer rate. However, it is relatively difficult to control the partial pressure of oxygen, and results are not as good as might be expected.

As yet another method, which does not involve the direct supply of air to the culture cells as do the methods described above, there is a method in which air is supplied indirectly with the use of a semi-permeable membrane or a silicone membrane. By this method, on one side of the membranes mentioned above, air or a liquid medium that contains air is caused to flow, and air is supplied through the membrane to the culture cells on the other side. For example, a method is disclosed in Japanese Laid-Open Patent Application No. 60-234580 in which oxygen is supplied to the culture broth via a semi-permeable membrane. However, in this method, the resistance of the membranes mentioned above is great when air is permeating through them. For that reason, in order to assure the amount of air needed for the growth of the cells, it is necessary for the surface area of the membranes to be extremely large, and a large culture vessel is needed. Moreover, the disposition of the membranes in the culture vessel becomes very complicated. In particular, when the culture involves the use of a microcarrier, the microcarrier that is carrying the cells comes to be distributed in a very uneven way throughout the culture vessel, so that the cells in the areas that are relatively undisturbed die. The structure of the culture vessel is complex, which has the drawback of being expensive. Therefore, the indirect aeration method that involves the use of a membrane is not appropriate for use in large culture vessels on the industrial scale.

As mentioned above, there have not been any effective means for the aeration of mammalian cells being cultured in a large-scale culture apparatus until now.

SUMMARY OF THE INVENTION

The aeration apparatus for the culture of mammalian cells of this invention, which overcomes the above-discussed and numerous other disadvantages and deficiencies of the prior art, comprises a number of bundles composed of thin-walled narrow tubes made of a gas-permeable material, and the aeration means for flowing air through the insides of said thin-walled narrow tubes.

In a preferred embodiment, the aeration means is composed of a number of individual parts, and each part is connected at one end thereof to a head for the introduction of air.

In a preferred embodiment, the aeration part is coupled at its other end to a head for the removal of air.

In a preferred embodiment, the thin-walled narrow tubes are made of silicone resin.

Thus, the invention disclosed herein makes possible the objectives of (1) providing an aeration apparatus that can supply sufficient air to mammalian cells being cultured in a culture vessel, thereby attaining efficient culture of the mammalian cells; (2) providing an aeration apparatus for use in the culture of mammalian cells that can be used either in large culture vessels on the industrial scale and in small culture vessels, said apparatus preventing both the inhibition of the growth of the cells and a decline in the production of products produced by the cells; (3) providing an aeration apparatus with a simple structure for the culture of mammalian cells with use of a microcarrier, which prevents cell death caused by the microcarrier being distributed in a very uneven way.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
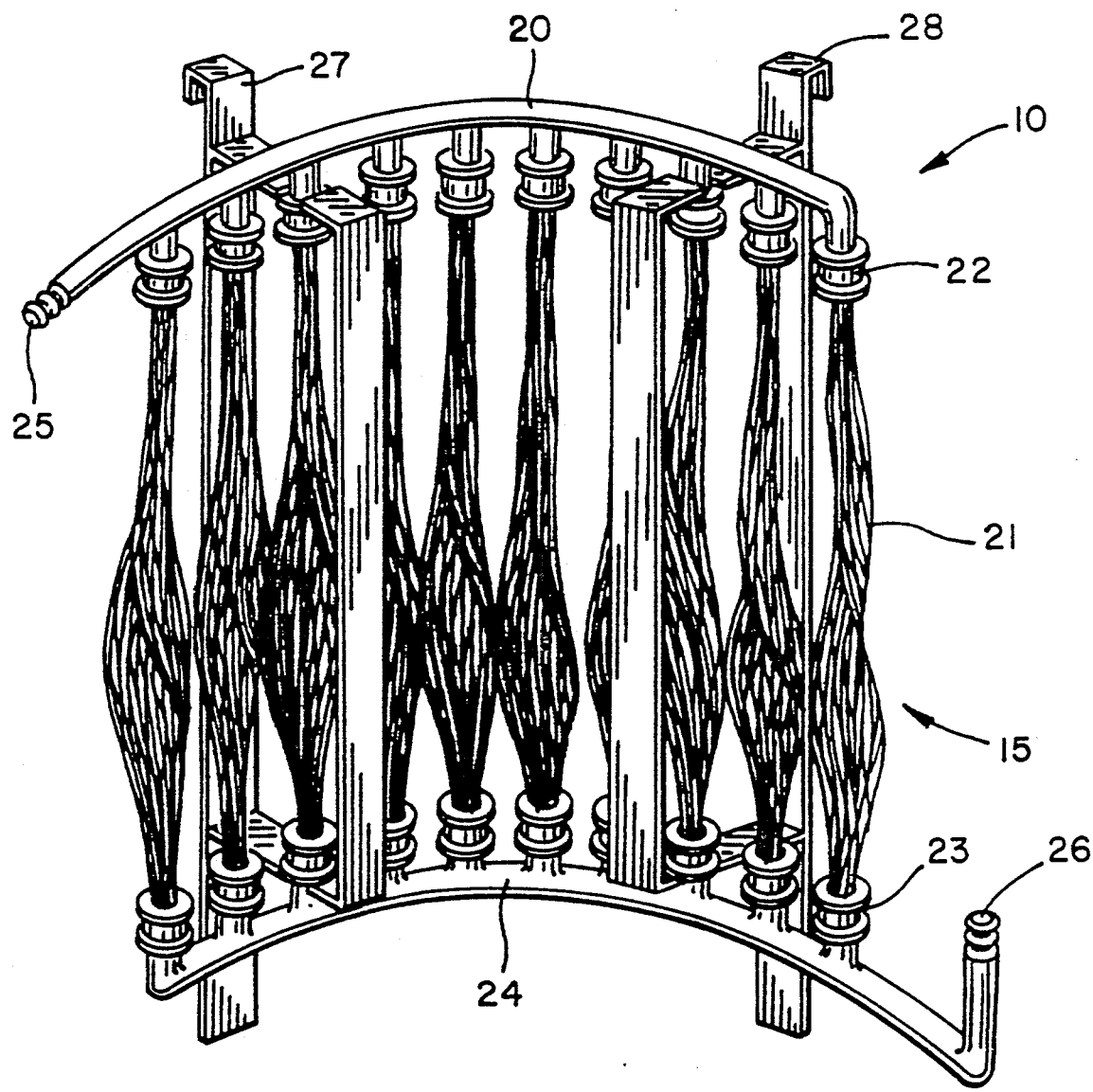
FIG. 1 is a perspective view showing an aeration apparatus for the culture of mammalian cells of this invention.
Figure 2:
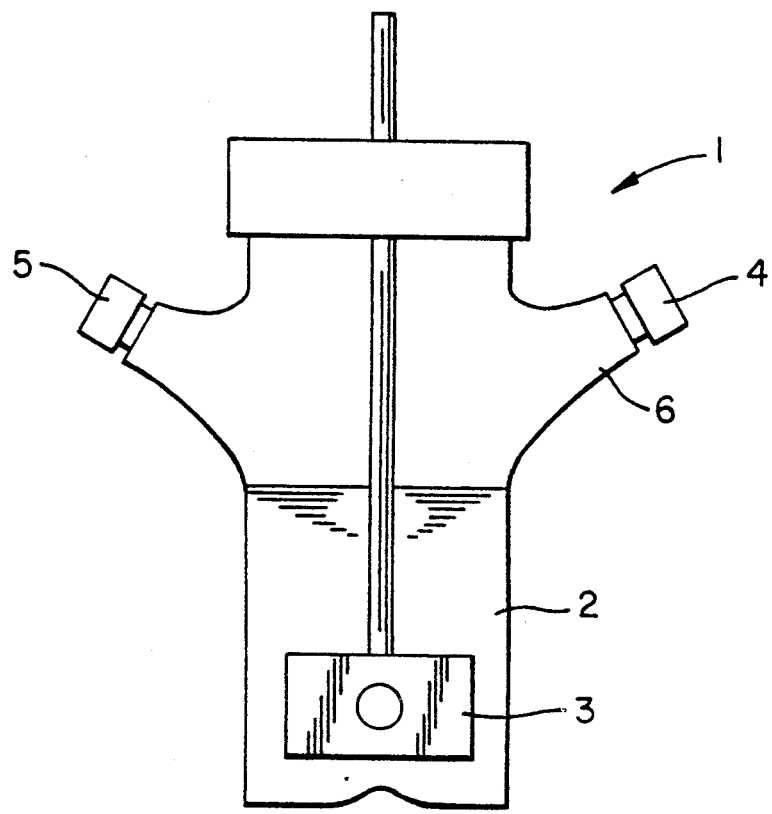
FIG. 2 is a schematic diagram showing a conventional culture apparatus for the culture of mammalian cells.
Figure 3:
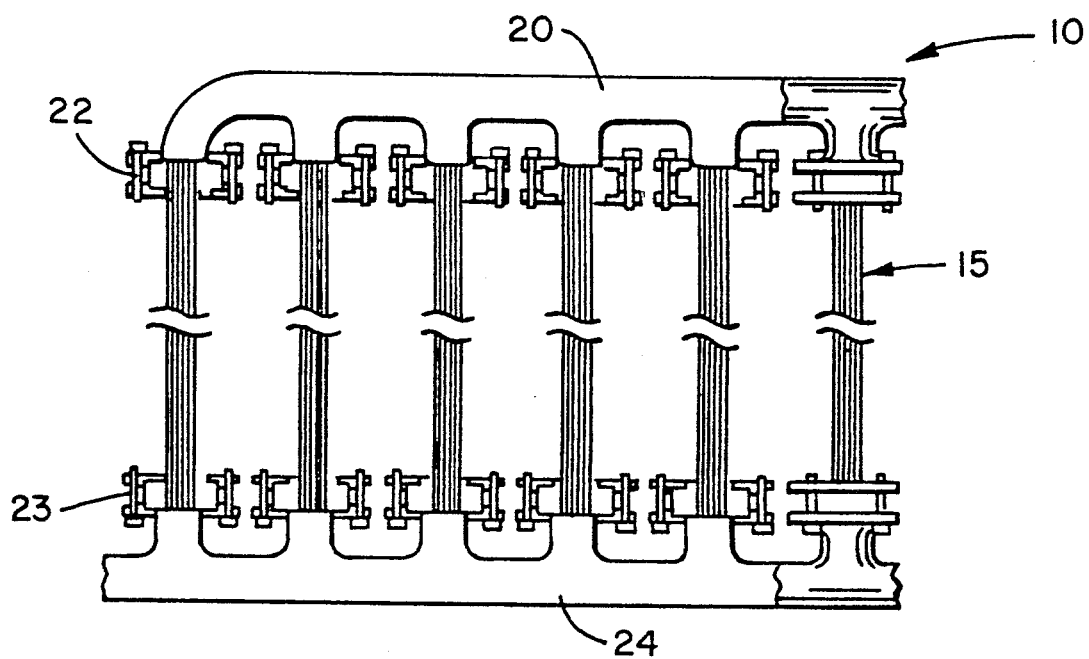
FIG. 3 is a sectional view showing a part of the apparatus of this invention shown in FIG. 1.

FIG. 1 shows an aeration apparatus 10 of this invention, which has a number of aeration means 15 that are composed of a number of bundles of thin-walled narrow tubes 21 that are made of a gas-permeable material. As shown in FIG. 3, one end of each of the aeration means 15 is connected with connectors 21 of a head 20 for use in the introduction of air. The other ends are connected with the connectors 23 of a head 24 for use in the removal of air. This example has ten aeration means 15, and each is attached to the heads 20 and 24 so that they are almost perpendicular. The head 20 for the introduction of air and the head 24 for the removal of air are curved so as to fit the inside shape of the culture vessel 1a (see FIGS. 4 and 5). The heads 20 and 24 are connected with each other by means of fixing means 27 and 28, by which the heads 20 and 24 are fixed to the culture vessel 1a.

Into the head 20 for the introduction of air, air flows from an air supply inlet 25. The air that flows into the head 20 disperses into the thin-walled narrow tubes 21 of each of the aeration means 15, and air passes through the thin-walled narrow tubes 21. One part of the air that flows inside the thin-walled narrow tubes 21 permeates through the tubes wall of the thin-walled narrow tubes 21, and flows out into the culture vessel 1a. The air that flows through the thin-walled narrow tubes 21 is collected by the head 24 for air exhaust and ejected from an air outlet 26 of the head 24 for air exhaust.

Figure 4:
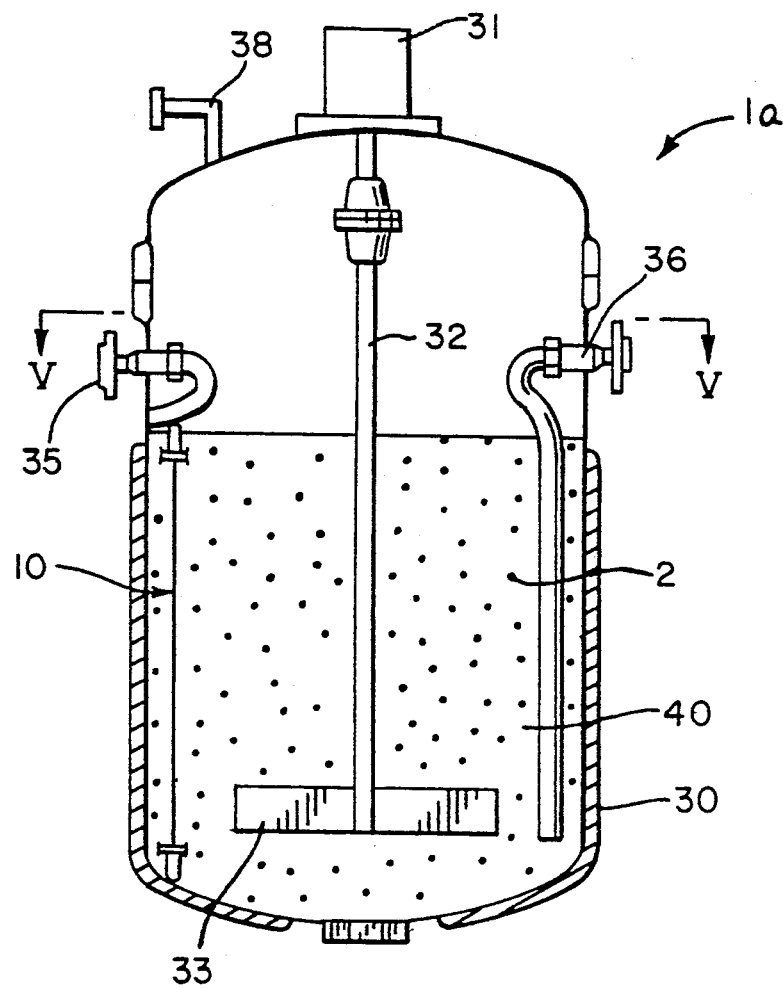
FIG. 4 is a sectional view showing the attachment of the aeration apparatus of this invention to a culture vessel.

Next, the situation in which this aeration apparatus 10 is put to actual use will be described. FIG. 4 shows the attachment of the aeration apparatus 10 to the culture vessel 1a. The heads 20 and 24 are fixed to the fixing means 27 and 28 mentioned before, and these fixing means 27 and 28 are attached to the inside wall of culture vessel 1a. In this way, the aeration apparatus 10 is fixed to the inside of culture vessel 1a. At this time, the air supply inlet 25 is connected via a connecting tube 41 to a control valve 42 on the side of the introduction of air, and the outlet 26 is connected via a connecting tube 43 to a control valve 44 on the side of the air exhaust. The thin-walled narrow tubes 21 of the aeration means 15 that are placed between the heads 20 and 24 are not pulled so as to be completely straight, but are allowed to curve slightly.

The culture vessel 1a contains culture broth 2, which contains either mammalian cells or microcarrier 40 that supports mammalian cells. A hot-water jacket 30 is provided around the outer surface of the culture vessel 1a, and used to control the culture temperature.

The culture vessel 1a is provided with other apparatuses to supply and remove culture broth, apparatuses to control the atmosphere, and apparatuses used to achieve continuous culture. For example, in the culture vessel 1a, a shaft 32 is placed almost vertically, and there is an impeller 33 at its lower end. The shaft 32 is driven by a motor drive 31 provided outside the culture vessel 1a. Moreover, in the culture vessel 1a, there is a culture broth removal outlet 34 for the removal of the culture broth from the culture vessel 1a; there is a culture broth supply inlet 35 provided for the purpose of supplying culture broth to the culture vessel 1a; there is a sample collection opening 36 from which the culture broth in the culture vessel 1a can be sampled; there is a gas exhaust outlet 28 for the removal of air, etc., from the inside of the culture vessel 1a; and so on.

Figure 5:
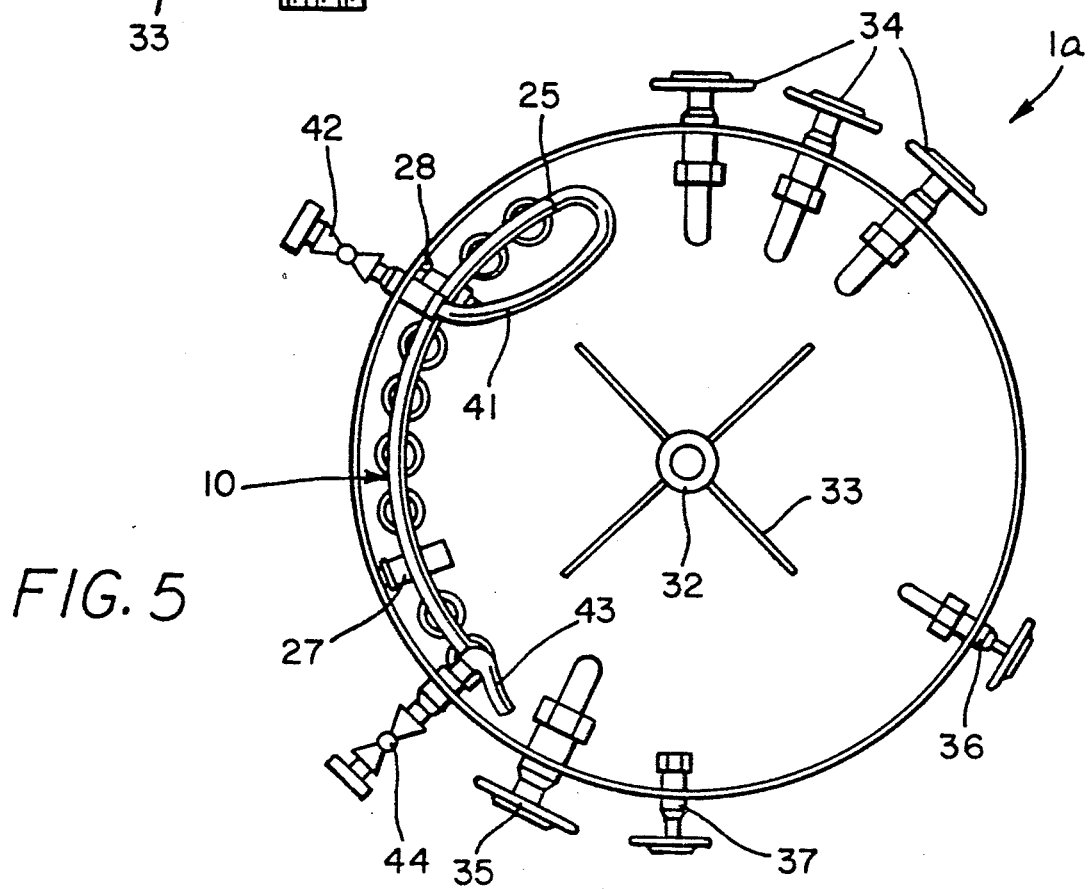
FIG. 5 is a sectional view along line V—V of FIG. 4.

To use the aeration device as it is shown in FIGS. 4 and 5, first, an adequate amount of culture broth 2 is used to fill the culture vessel so that the aeration apparatus 10 can be completely submerged. Then, the control valve 42 for the introduction of air is set to the 'open' position. In this way, air is allowed to enter into the aeration apparatus 10. At this time, air is allowed to fill the inside of the thin-walled narrow tubes 21 by the adjustment of the control valve 44 for the removal of air, and pressure is brought to bear on the said air. Thus, the air in the thin-walled narrow tubes 21 passes through the walls of the thin-walled narrow tubes 21 to be dissolved into the culture broth 2. The thin-walled narrow tubes 21 are in a slightly bent position, so when air is being dissolved to the culture broth 2 from the thin-walled narrow tubes 21, the thin-walled narrow tubes become untidy, being curved like seaweed in the sea. Therefore, the air that permeates through the thin-walled narrow tubes 21 is adequately diffused throughout the culture broth. Since the aeration means 15 of this aeration apparatus 10 are composed of bundles of thin-walled narrow tubes 21, their volume is relatively small, and not much space is taken up inside the culture vessel 1a.

For the aeration apparatus 10 to supply air into the culture cells 2, it is necessary to exert a fixed amount of pressure on the air that is inside the thin-walled narrow tubes 21, as mentioned above. In the example given above, adjustment of the control valve 44 on the side of the removal of air makes it possible to change the pressure exerted on the air that is in the thin-walled narrow tubes 21.

The material of which the thin-walled tubes 21 are made should be one that is satisfactorily permeable to air. When the consideration is made that the thin-walled narrow tubes 21 are used with the aeration apparatus 10 attached to the culture vessel 1a, it is preferable that they be sterilizable by steam under pressure. As thin-walled narrow tubes 21 that fulfill these requirements, silicone resin tubes (i.e., silicone tubes) are most suitable. In apparatus that are described in DESCRIPTION OF THE PRIOR ART, semipermeable membranes and silicone membranes that are permeable to air are also used, but these are used in flat shapes, so resistance to the movement of air is great, and air does not permeate through them effectively. In comparison, in this invention, thin tubes that are permeable to gases are used, so the gas pressure of the air is equal around the circumference of the said thin tubes, and for that reason, air permeates through with relative ease.

The length of the thin-walled tubes 21 varies depending on the size, shape, and capacity of the culture vessel 1a; the length is set so that the entire aeration apparatus 10 will be immersed into the culture broth 2 to be put into the culture vessel 1a. The numbers of thin-walled narrow tubes 21 used to make the aeration means 15 and the numbers of aeration means 15 that are used to constitute the aeration apparatus 10 are not limited to the numbers shown in the example. The numbers of tubes are decided so as to be suitable based on the volumetric oxygen-transfer coefficient needed for the entire aeration apparatus 10 and based on the shape and capacity of the culture vessel 1a. When thin-walled narrow tubes with a suitable length are bundled to make a number of aeration means, the aeration apparatus mentioned above with a simplified structure can be obtained, which can supply the necessary and sufficient air for the growth of mammalian cells without giving rise to bubbles.

The inventors of this invention have studied the durability of the aeration apparatus 10 to steam sterilization under pressure, its resistance to pressure, damage caused by operation, and the like, and have calculated the volumetric oxygen-transfer coefficient for the aeration apparatus 10, as well as carrying out various tests on an industrial scale (about 500 liters) of the construction of appropriate aeration means 15 for the culture vessel 1a. The results showed that when thin-walled narrow tubes 21 made of silicone resin and 60-150 cm long were used in the culture, each aeration means 15 should have 300-600 thin-walled narrow tubes 21, and the inner diameter of the thin-walled narrow tubes should be in the range of 0.1 to 1.0 mm, with the outer diameter in the range of 0.2 to 2.0 mm, in order to get the optimum results.

Figure 6:
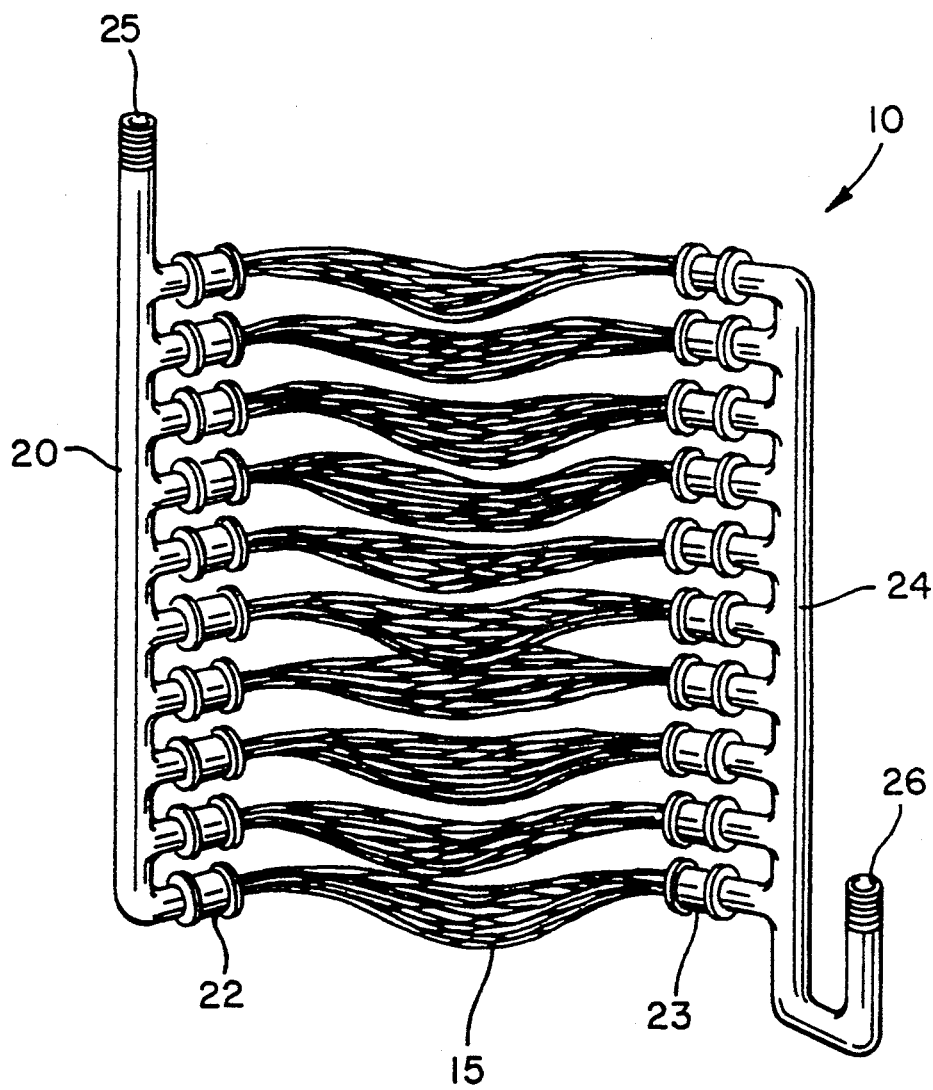
FIG. 6 is a perspective view showing another aeration apparatus for the culture of mammalian cells of this invention.

The above-mentioned example describes the aeration apparatus 10 with the thin-walled narrow tubes 21 stretched upward and downward, but this invention is not limited thereto For example, as shown in FIG. 6, the aeration apparatus 10 can be constituted by the aeration means 15 that are composed of the thin-walled narrow tubes 21 placed almost horizontal. In this case, results like those given above can be obtained.

With the use of the apparatus (with a capacity of 500 liters) disclosed in FIG. 4, mouse C127 cells were put on a microcarrier and cultured. As the medium, Dulbecco's minimum essential medium (DMEM) was used with the addition of 10% fetal calf serum. As the microcarrier, Cytodex 3 (Pharmacia, Inc.,) was used, added to the medium at the concentration of 6 g/l. The cells were cultured for 4 days at 37° C. The maximum concentration of cells reached was $5 \times 10^6$ cells/ml.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. An aeration apparatus for culturing mammalian cells in a large-scale culture vessel comprising a plurality of aeration means, each of said aeration means comprising a bundle of thin-walled narrow tubes made of a gas permeable material, first head means for introducing a gas, first connector means providing flow communication between said first head means and said bundle of tubes at a first end of each of said aeration means, second head means for removing a gas and second connector means providing flow communication between said second head means and said bundle of tubes at a second end of each of said aeration means, said first head means and said second head means including fixing means for positioning said aeration apparatus to the inside of the culture vessel such that said thin-walled narrow tubes of said aeration means are positioned between said first head means and said second head means along the inside surface of the vessel so as to be slackened, so that said thin-walled narrow tubes are capable of waving in the vessel when gas or air is supplied to said aeration means.

2. An aeration apparatus according to claim 1, wherein said thin-walled narrow tubes are made of silicone resin.

* * * * *

UNITED STATES PATENT AND TRADEMARK OFFICE
CERTIFICATE OF CORRECTION

PATENT NO.  :  5,110,741
DATED       :  May 5, 1992
INVENTOR(S) :  Kiyomoto Ohi and Shin Shimizu It is certified that error appears in the above-identified patent and that said Letters Patent is hereby corrected as shown below:

Column 1, line 63, change "product" to

-- products --; and

Column 3, line 30, change "21" to -- 22 --.

Signed and Sealed this

Twenty-ninth Day of June, 1993

Attest:

MICHAEL K. KIRK

*Attesting Officer*           Acting Commissioner of Patents and Trademarks